US00PP25903P3

(12) United States Plant Patent

Mori et al.

(10) Patent No.: US PP25,903 P3

(45) Date of Patent: Sep. 15, 2015

(54) *GOMPHRENA* PLANT NAMED 'SAKGOM003'

(50) Latin Name: *Gomphrena globosa*
Varietal Denomination: SAKGOM003

(71) Applicant: Sakata Seed Corporation, Yokohama (JP)

(72) Inventors: Kazutoshi Mori, Matsumoto (JP); Masatoshi Tanaka, Kanagawa (JP)

(73) Assignee: Sakata Seed Corporation, Yokohama (JP)

( * ) Notice: Subject to any disclaimer, the term of this patent is extended or adjusted under 35 U.S.C. 154(b) by 103 days.

(21) Appl. No.: 13/999,155

(22) Filed: Jan. 21, 2014

(65) Prior Publication Data

US 2015/0208565 P1 Jul. 23, 2015

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Annette Para
(74) *Attorney, Agent, or Firm* — James M. Weatherly; Barbara Campbell; Cochran Freund & Young LLC

(57) ABSTRACT

A *Gomphrena* plant particularly distinguished by having a white flowers and a spreading plant growth habit, is disclosed.

1 Drawing Sheet

Genus and species: *Gomphrena globosa.*
Variety denomination: 'SAKGOM003'.

BACKGROUND OF THE NEW PLANT

The present invention comprises of a new and distinct variety of *Gomphrena,* botanically known as *Gomphrena globosa,* and referred to by the variety name 'SAKGOM003'. 'SAKGOM003' originated from a controlled cross in July 1998 in Misato, Japan between the proprietary female *Gomphera* breeding line '95G-11A-6E-1' (unpatented) having white flowers and a semi-creeping plant growth habit and the proprietary male *Gomphera* breeding line '95G-11A-2A-3' (unpatented) having magenta flowers and a semi-creeping plant growth habit. Thirty $F_1$ seeds were obtained and evaluated from the original cross.

In April 1999, the thirty $F_1$ seeds were sowed and three plants were cultivated. In July 1999, three plants were then chosen having a purple flower color. Between July 1999 and February 2009, seeds from the three chosen plants were cross-pollinated and seeds were obtained. In February 2009, 2000 seeds were sowed and 1000 plants were cultivated based on whether plants had purple flowers, purple flowers with white tips, and white flowers and whether plants had an upright plant growth habit or a spreading plant growth habit. In April 2009, a single plant was selected from this group having white flowers and a spreading plant growth habit.

From May 2009 to December 2009, the selection was evaluated in an open field in Misato, Japan. Vegetative cuttings of the variety were then shipped to Salinas, Calif., where the plants were regenerated and reevaluated for stability of traits. The selection subsequently was named 'SAKGOM003' and was found to have its unique characteristics reproduce true to type in successive generations of asexual propagation via vegetative cuttings.

SUMMARY

The following are the most outstanding and distinguishing characteristics of this new variety when grown under normal horticultural practices in Salinas, Calif.

1. White flowers; and
2. A spreading plant growth habit.

DESCRIPTION OF THE PHOTOGRAPHS

This *Gomphrena* plant is illustrated by the accompanying photographs which show the plant's overall plant habit including form, foliage, and flowers. The photographs are of plants grown about two-months-old in Salinas, Calif. under greenhouse conditions in the spring of 2013. The colors shown are as true as can be reasonably obtained by conventional photographic procedures.

DESCRIPTION OF THE NEW VARIETY

Figure 1:
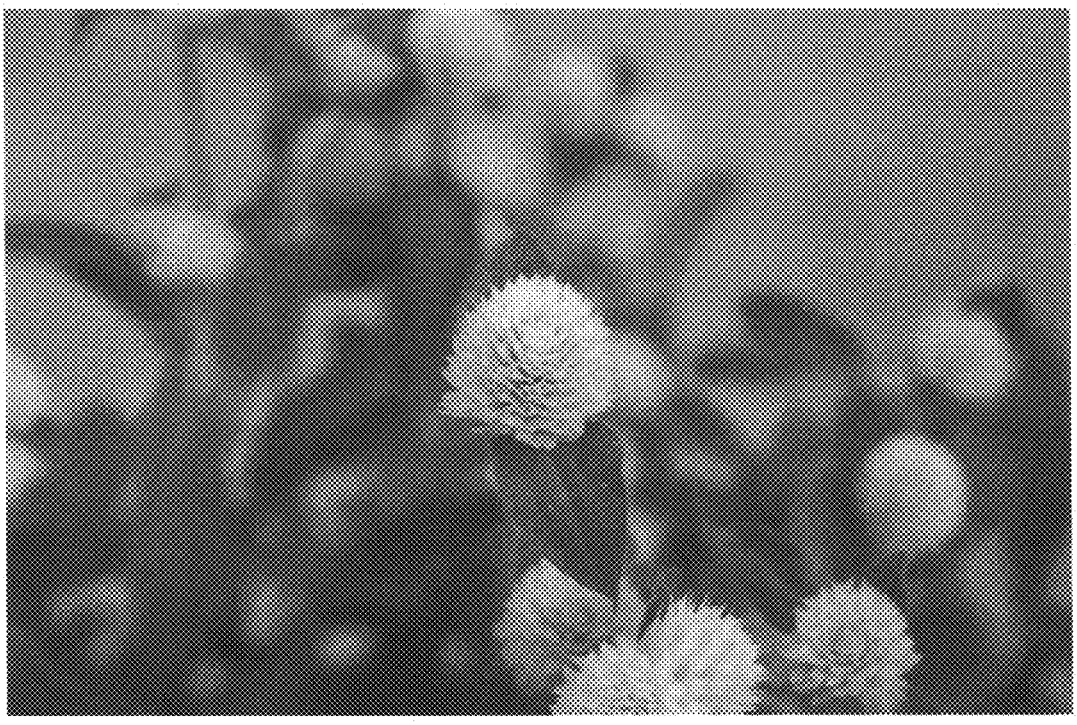
FIG. 1 shows a close-up of the mature flowers of the plant.
Figure 2:
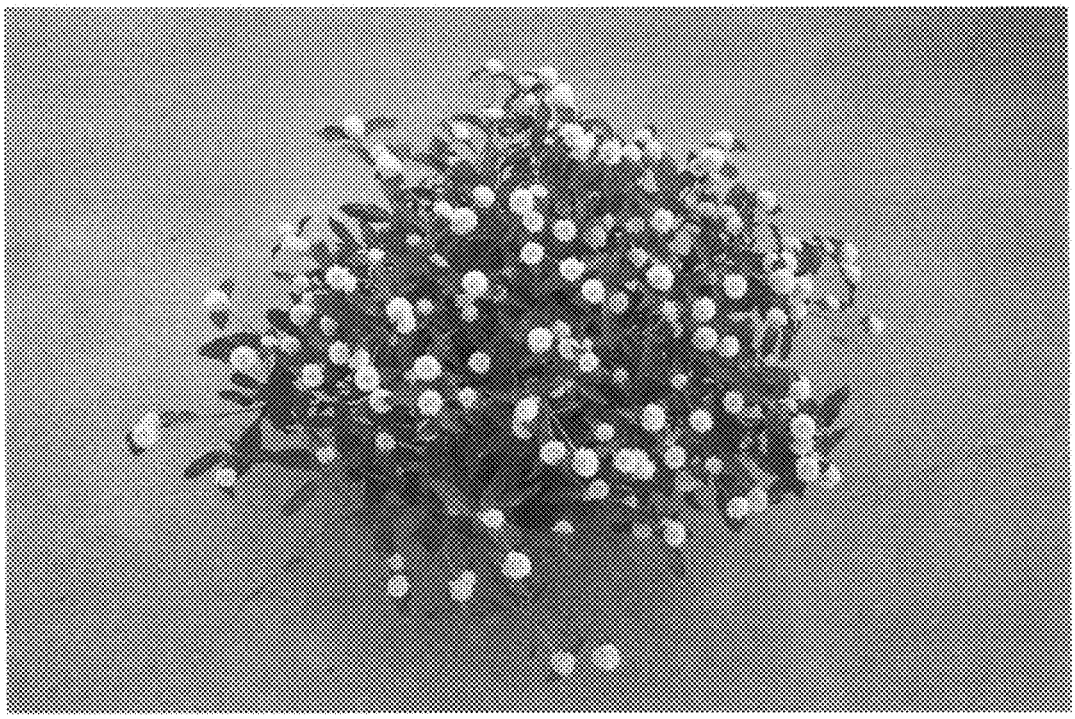
FIG. 2 shows the overall plant habit of the plant grown in a pot.

The following detailed descriptions set forth the distinctive characteristics of 'SAKGOM003'. The data which define these characteristics were collected from asexual reproductions carried out in Salinas, Calif. Data was collected on two-month-old plants under greenhouse conditions in Salinas, Calif. in the summer of 2013. Color references are to The R.H.S. Colour Chart of The Royal Horticultural Society of London (R.H.S.), $4^{th}$ edition (2001).

Classification:

*Family.*—Amaranthaceae.
*Botanical.*—*Gomphrena globosa.*
*Common.*—Globe amaranth.
*Designation.*—'SAKGOM003'.

Parentage:

*Female parent.*—Proprietary *Gomphrena* line '95G-11A-6E-1' (unpatented).
*Male parent.*—Proprietary *Gomphrena* line '95G-11A-2A-3' (unpatented).

Growth:

*Time to produce a rooted cutting.*—2 weeks.

*Environmental conditions for plant growth.*—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water), a root inducing solution, immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 14% nitrogen, 14% phosphorus and 14% potassium. The typical average air temperature was 24° C.

*Time to bloom from propagation.*—6 to 8 weeks.

Plant description:

*Habit.*—Spreading, upright, freely branching.

*Form.*—Prostrate.

*Life cycle.*—Annual.

*Height (from soil line to top of foliage).*—24.0 cm; 1.0 cm from soil line to first node.

*Spread.*—45.0 cm.

*Flowering requirements.*—Spring to fall, will flower year round at temperatures of 24 to 35° C.

Stems:

*Description.*—Dull, circular in cross section.

*Quantity.*—Numerous.

*Stem length.*—12.0 cm.

*Diameter.*—0.2 cm.

*Internode length.*—6.0 cm.

*Color.*—RHS 138A (Green) with RHS N79A (Purple).

*Pubescence.*—Heavy, long, hair-like, RHS N155A (White).

*Anthocyanin color.*—RHS N79A (Red-Purple).

Branches:

*Quantity.*—3 main.

*Description.*—Dull, circular in cross-section.

*Color.*—RHS 138A (Green) with RHS N79A (Purple).

*Anthocyanin.*—RHS N79A (Red-Purple).

*Pubescence.*—Heavy, long, hair-like, RHS N155A (White).

*Length.*—6.0 cm.

*Diameter.*—0.3 cm.

*Internode length.*—3.0 cm.

Leaves:

*Arrangement.*—Alternate.

*Shape.*—Lanceolate.

*Apex.*—Acute.

*Base.*—Decurrant.

*Margin.*—Entire.

*Surface pubescence (both surfaces?).*—Dull, moderately pubescent RHS N155A (White).

*Length.*—6.0 cm.

*Width.*—2.2 cm.

*Color.*—Upper surface: RHS 147A (Yellow-Green). Lower surface: RHS 147B (Yellow-Green).

*Venation.*—Pinnate.

*Fragrance.*—Absent.

Inflorescence:

*Type and appearance.*—Small, globose-shaped bracts; small flat flowers arranged in dense, globose, papery textured clover-live flower heads, flowers are upright and outwardly facing; flowers are sessile with a single two-parted perianth; inflorescence heads are subtended by two small flower bracts.

*Total number of flowers per plant.*—Approximately 150.

*Number of flowers per inflorescence.*—80 to 100.

*Flowering habit.*—Freely flowering.

*Lastingness of individual blooms on the plant.*—Approximately 4 weeks.

*Fragrance.*—Absent.

*Inflorescence height.*—2.0 cm.

*Inflorescence depth.*—1.5 cm.

*Inflorescence color.*—RHS 157A (Green-white).

*Flower height.*—0.7 cm.

*Flower diameter.*—0.3 cm.

*Sepals.*—None observed.

Flower bud:

*Surface texture.*—Dull, glabrous.

*Length.*—0.9 cm.

*Diameter.*—0.5 cm.

*Shape.*—Lanceolate.

*Color.*—RHS 157A (Green-white).

Bracts:

*Quantity.*—2.

*Arrangement.*—Opposite.

*Length.*—0.6 cm.

*Width.*—0.2 cm.

*Shape.*—Lanceolate.

*Apex.*—Acute.

*Texture.*—Dull, glabrous.

*Color.*—RHS 157A (Green-white).

Peduncle:

*Length.*—6.5 cm.

*Diameter.*—0.1 cm.

*Angle.*—Mostly upright to 40° vertical.

*Strength.*—Strong, moderately.

*Color.*—RHS 138A (Green).

*Surface texture and appearance.*—Dull, moderate pubescence, RHS N155A (White).

Reproductive organs:

*Stamen number.*—5 per flower.

*Stamen color.*—RHS N155A (White).

*Stamen length.*—0.4 cm.

*Filament length.*—0.3 cm.

*Filament color.*—RHS 143A (Green).

*Anther length.*—0.5 cm.

*Anther color.*—RHS 155A (White).

*Pollen color.*—RHS 155A (White).

*Pollen amount.*—Sparse.

*Ovary diameter.*—0.1 cm.

*Ovary surface color.*—RHS 143A (Yellow-green).

*Pistil number.*—1 per inflorescence.

*Pistil length.*—0.6 cm.

*Stigma shape.*—Bi-parted.

*Stigma color.*—RHS 157A (Green-white).

*Style length.*—0.5 cm.

*Style color.*—RHS 157A (Green-white).

*Seed production.*—Absent.

*Fragrance.*—Absent.

Disease and insect resistance: No unusual susceptibility or resistance to diseases or insects has been observed.

COMPARISON WITH PARENTAL LINES AND KNOWN VARIETY

'SAKGOM003' is a new and unique variety of *Gomphrena* owing to its white flower color and spreading plant growth habit. 'SAKGOM003' is distinguished from its parents mainly by flower color and habit as shown in Table 1 below:

TABLE 1

Comparison with Parental Lines

| Characteristic | 'SAKGOM003' | Female Parent '95G-11A-6E-1' | Male Parent '95G-11A-2A-3' |
|---|---|---|---|
| Flower color | White | White | Magenta |
| Habit | Spreading | Semi-creeping | Semi-creeping |

'SAKGOM003' is a new and unique variety of *Gomphrena* owing to its white flowers. When 'SAKGOM003' is compared to the commercial *Gomphrena* variety 'Balboa' (U.S. Plant Pat. No. 22,263) the difference is described in the table below.

TABLE 2

Comparison with Similar Variety

| Characteristic | 'SAKGOM003' | 'Balboa' |
|---|---|---|
| Flower color | White | Purple |

We claim:

1. A new and distinct cultivar of *Gomphrena* plant as shown and described herein.

* * * * *